United States Patent [19]

Manero et al.

[11] Patent Number: 5,942,618
[45] Date of Patent: Aug. 24, 1999

[54] 1-FLUOR-5,6,7,8-TETRAHYDROISOQUINOLINE DERIVATIVES, AND THEIR USE IN LIQUID-CRYSTAL LINE MIXTURES

[75] Inventors: Javier Manero, Frankfurt; Rainer Wingen, Hattersheim, both of Germany

[73] Assignee: Hoechst Aktiengesellschaft, Frankfurt, Germany

[21] Appl. No.: 08/952,125

[22] PCT Filed: May 10, 1996

[86] PCT No.: PCT/EP96/01995

§ 371 Date: Nov. 6, 1997

§ 102(e) Date: Nov. 6, 1997

[87] PCT Pub. No.: WO96/35675

PCT Pub. Date: Nov. 14, 1996

[30] Foreign Application Priority Data

May 10, 1995 [DE] Germany .................. 195 17 056

[51] Int. Cl.$^6$ .................. C07D 217/22; C07D 401/04; C09K 19/34
[52] U.S. Cl. .................. 546/139; 252/299.01; 544/333; 546/148
[58] Field of Search .................. 546/139, 148; 252/299.01; 544/333

[56] References Cited

FOREIGN PATENT DOCUMENTS

| 0643119A1 | 3/1995 | European Pat. Off. . |
| WO 92/11241 | 7/1992 | WIPO . |

OTHER PUBLICATIONS

Ferroelectrics, 1993, vol. 148, p. 139 ff.

*Primary Examiner*—Zinna Northington Davis
*Attorney, Agent, or Firm*—Frommer Lawrence & Haug LLP

[57] ABSTRACT

1-Fluoro-5,6,7,8-tetrahydroisoquinoline derivatives, and their use in liquid-crystalline mixtures 1-Fluoro-5,6,7,8-tetrahydroisoquinoline derivatives of the formula (I)

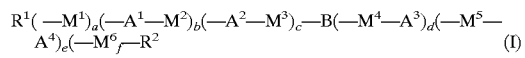

in which the symbols and indices have the following meanings:

the group B is

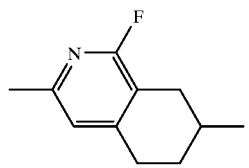

$R^1$ and $R^2$ are, for example, alkyl radicals having 1 to 20 carbon atoms;

$M^1$, $M^2$, $M^3$, $M^4$, $M^5$ and $M^6$ are, for example, —O—, —CO—O—, —O—CO— or a single bond;

$A^1$, $A^2$, $A^3$ and $A^4$ are, for example, 1,4-phenylene, pyrimidine-2,5-diyl or trans-1,4-cyclohexylene, and a, b, c, d, e and f are zero or one, with the proviso that the sum of b, c, d and e is 0, 1 or 2.

The compounds of the formula (I) are colorless in the pure state and generally form liquid-crystalline mesophases in a temperature range which is favorably located for electro-optical use. They are stable chemically, thermally and to light.

9 Claims, No Drawings

1-FLUOR-5,6,7,8-TETRAHYDROISOQUINOLINE DERIVATIVES, AND THEIR USE IN LIQUID-CRYSTAL LINE MIXTURES

This application is a 371 of PCT/EP96/01995 filed May 10, 1995.

In addition to nematic and cholesteric liquid crystals, optically active tilted smectic (ferroelectric) liquid crystals have also been used recently in commercial display devices.

Clark and Lagerwall have been able to show that the use of ferroelectric liquid crystals (FLCs) in very thin cells results in optoelectrical switching or display elements which have response times faster by a factor of up to 1000 compared with conventional TN ("twisted nematic") cells (see, for example, EP-A 0 032 362). On the basis of this and other favorable properties, for example the possibility of bistable switching and the virtually viewing angle-independent contrast, FLCs are fundamentally highly suitable for areas of application such as computer displays.

For the use of FLCs in electro-optical or fully optical components, either compounds are required which form tilted or orthogonal smectic phases and are themselves optically active, or ferroelectric smectic phases can be induced by doping compounds which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S^*_C$ phase can be achieved, for example, if the phase sequence of the liquid-crystal mixture is, with decreasing temperature:

isotropic→N*→$S_A$→$S^*_C$

The prerequisite is that the pitch of the helix in the N* phase is very large (greater than 10 μm) or, even better, is fully compensated (see, for example, T. Matsumoto et al., pp. 468–470, Proc. of the 6th Int. Display Research Conf., Japan Display, Sep. 30–Oct. 2, 1986, Tokyo, Japan; M. Murakami et al., ibid. pp. 344–347). This is achieved by adding one or more optically active dopes which induce a right-hand helix to the chiral liquid-crystal mixture which has, for example, a left-hand helix in the N* phase, in such amounts that the helix is compensated.

A further prerequisite for the use of the SSFLCD effect (surface-stabilized ferroelectric liquid-crystal display) of Clark and Lagerwall for uniform planar alignment is that the pitch in the smectic C* phase is significantly greater than the thickness of the display element (Mol. Cryst. Liq. Cryst. 94 (1983), 213-134 and 114 (1984), 151–187). As in the case of the cholesteric pitch, this is achieved by using dopes having the opposite rotation of the helix.

The optical response time T [μS] of ferroelectric liquid-crystal systems, which should be as short as possible, depends on the rotational viscosity of the system y[mPas], the spontaneous polarization $P_s$[nC/cm²] and the electric field strength E[V/m], in accordance with the equation $$\tau \sim \frac{\gamma}{P_s \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn, preferably=0.13, and a low positive or preferably negative dielectric anisotropy Δε are required (see, for example, S. T. Lagerwall et al., "Ferroelectric Liquid Crystals for Displays", SID Symposium, Oct. Meeting 1985, San Diego, Calif., USA). The totality of these requirements can only be achieved by means of mixtures comprising a plurality of components. The base (or matrix) used preferably comprises compounds which if possible themselves already have the desired phase sequence I→N→$S_A$→$S_C$. Further components of the mixture are frequently added in order to reduce the melting point and to broaden the $S_C$ and usually also the N phase, to induce optical activity, for pitch compensation and to match the optical and dielectric anisotropy; further, the rotational viscosity, for example, should if possible not be increased.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff.; the PSFLCD effect is described in DE-A 39 20 625 and EP-A 0 405 346. In contrast to the SSFLCD effect, utilization of these effects requires a liquid-crystalline material having a short $S_C$ pitch.

Quinoline and isoquinoline derivatives for use in liquid-crystal mixtures are disclosed, for example, in Ferroelectrics 148,1993, 139-45 and EP-A 0 643 119.

However, since the development of ferroelectric liquid-crystal mixtures in particular can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

The object of the present invention was therefore to provide novel compounds which are suitable in liquid-crystalline mixtures for improving the property profile of these mixtures.

It has now been found, surprisingly, that 3,7-disubstituted 1-fluoro-5,6,7,8-tetrahydroisoquinoline derivatives of the formula (I) are particularly suitable for use in liquid-crystal mixtures.

The invention therefore relates to compounds of the formula (I)

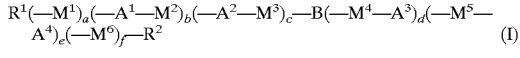

$R^1(-M^1)_a(-A^1-M^2)_b(-A^2-M^3)_c-B(-M^4-A^3)_d(-M^5-A^4)_e(-M^6)_f-R^2$ (I)

in which the symbols and indices have the following meanings: the group B is

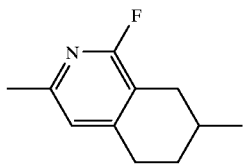

$R^1$ and $R^2$ are identical or different and are hydrogen, —CN, —F, —Cl, —CF₃, —CHF₂, —CH₂F, —OCF₃, —OCHF$_2$, —OCH$_2$F or a straight-chain or branched alkyl radical having 1 to 20 carbon atoms (with or without an asymmetrical carbon atom), where one or more CH$_2$ groups may also be replaced by —O—, —S—, —CO—O—, —O—CO—, —O—CO—O—, —CO—, —CS—, —CH=CH—, —C≡C—, cyclopropane-1,2-diyl, —Si(CH$_3$)$_2$—, 1,4-phenylene, trans-1,4-cyclohexylene or trans-1,3-cyclopentylene, with the proviso that oxygen atoms and/or sulfur atoms must not be bonded directly to one another, and/or where one or more H atoms of the alkyl radical may be substituted by —F—, —Cl, —Br, —OR$^3$, —SCN, —OCN or —N$_3$, or are alternatively one of the following groups (optically active or racemic):

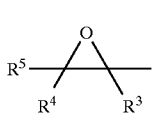 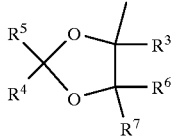

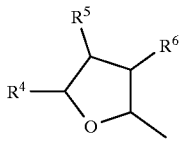 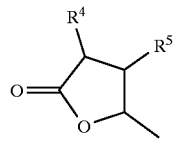

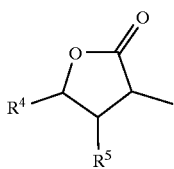 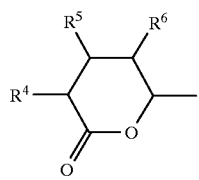

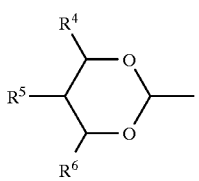 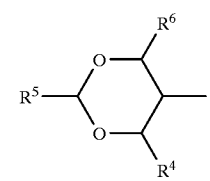

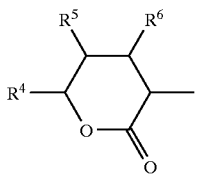 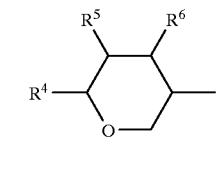

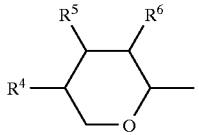 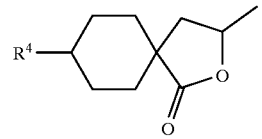

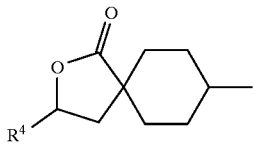 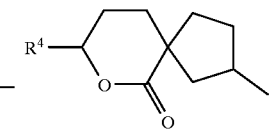

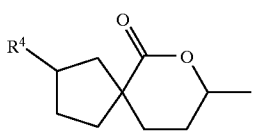

-continued

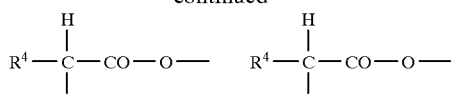

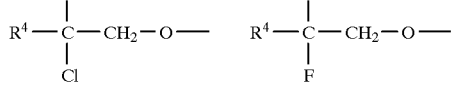

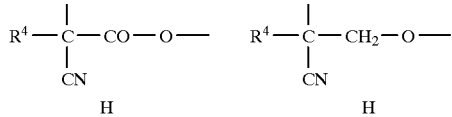

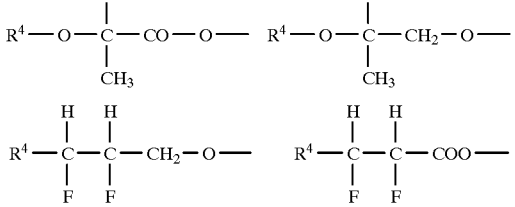

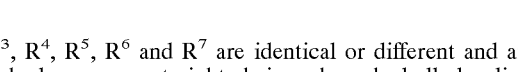

R$^3$, R$^4$, R$^5$, R$^6$ and R$^7$ are identical or different and are hydrogen or a straight-chain or branched alkyl radical having 1–16 carbon atoms (with or without an asymmetrical carbon atom), where one or more CH$_2$ groups may also be replaced by —O— and/or —CH=CH—, with the proviso that oxygen atoms must not be bonded directly to one another, and/or where one or more H atoms of the alkyl radical may be substituted by —F or —Cl; R$^4$ and R$^5$ may also together be —(CH$_2$)$_4$— or —(CH$_2$)$_5$— if they are bonded to an oxirane, dioxolane, tetrahydrofuran, tetrahydropyran, butyrolactone or valerolactone system;

M$^1$, M$^2$, M$^3$, M$^4$, M$^5$ and M$^6$ are identical or different and are —O—, —S—, —CO—, —CO—O—, —O—CO—, —O—CO—O—, —CO—S—, —S—CO—, —CS—O—, —O—CS—, —S—CS—S—, —O—CS—O—, —S—CO—S—, —CS—, —CH$_2$—O—, —O—CH$_2$—, —CH$_2$—S—, —S—CH$_2$—, —CH=CH—, —C≡C—, —CH$_2$—CH$_2$—CO—O, —O—CO—CH$_2$—CH$_2$—, or a single bond;

A$^1$, A$^2$, A$^3$ and A$^4$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH$_3$, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, piperazine-1,4-diyl, piperazine-2,5-diyl, naphthalene-2,6-diyl, in which one or more H atoms may be replaced by F, Cl and/or CN, bicyclo[2.2.2]octane-1,4-diyl, in which one or more H atoms may be replaced by F, Cl and/or CN, 1,3-dioxaborinane-2,5-diyl or the group B;

a, b, c, d, e and f are zero or one, with the proviso that the sum of b, c, d and e must be 0, 1 or 2.

In the pure state, the compounds of the formula (I) are colorless and generally form liquid-crystalline mesophases in a temperature range which is favorably located for electro-optical use. They are stable chemically, thermally and to light.

The compounds of the formula (I) are particularly suitable, even when added in small amounts, for modifying the dielectric anisotropy $\Delta\epsilon$ of liquid-crystalline mixtures in the direction of greater negative values.

Preference is given to compounds of the formula (I) in which the symbols and indices have the following meanings:

$R^1$ and $R^2$ are identical or different and are hydrogen, —CN, —F, —Cl, —CF$_3$, —CHF$_2$, —CH$_2$F, —OCF$_3$, —OCHF$_2$, —OCH$_2$F or a straight-chain or branched alkyl radical having 1 to 18 carbon atoms (with or without an asymmetrical carbon atom), where one or more CH$_2$ groups may also be replaced by —O—, —CO—, —CO—O—, —O—CO—, —O—CO—O—, —CH=CH—, —C≡C—, cyclopropane-1,2-diyl, —Si(CH$_3$)$_2$— or trans-1,4-cyclohexylene, with the proviso that oxygen atoms must not be bonded directly to one another, and/or where one or more H atoms of the alkyl radical may be substituted by —F, —Cl, —OR$^3$, —OCN or —N$_3$, or are one of the following groups (optically active or racemic):

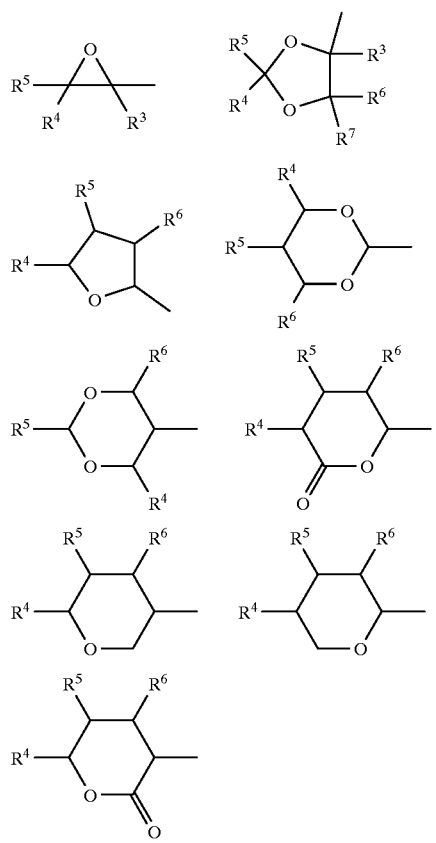

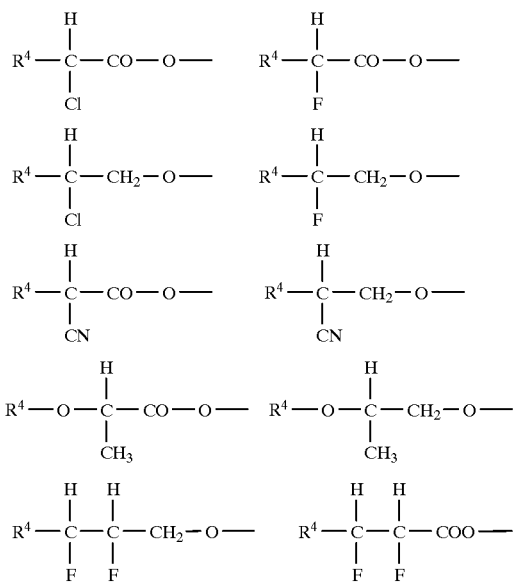

$R^3$, $R^4$, $R^5$, $R^6$ and $R^7$ are identical or different and are hydrogen or a straight-chain or branched alkyl radical having 1–16 carbon atoms (with or without an asymmetrical carbon atom), where one or more CH$_2$ groups may also be replaced by —O— and/or —CH=CH—, with the proviso that oxygen atoms must not be bonded directly to one another, and/or where one or more H atoms of the alkyl radical [Not to be taken into consideration for the purposes of international processing]

$R^1$ and $R^2$ are identical or different and are hydrogen, —CN, —F, —Cl, —CF$_3$, —CHF$_2$, —CH$_2$F, —OCF$_3$, —OCHF$_2$, —OCH$_2$F or a straight-chain or branched alkyl radical having 1 to 16 carbon atoms (with or without an asymmetrical carbon atom), where one, two or three CH$_2$ groups may also be replaced by —O—, —CO—, —O—CO—, —CO—O—, —CH=CH—, cyclopropane-1,2-diyl, —Si(CH$_3$)$_2$— or trans-1,4-cyclohexylene, with the proviso that oxygen atoms must not be bonded directly to one another, and/or where one or more H atoms of the alkyl radical may be substituted by —F, —Cl or —OR$^3$, or are alternatively one of the following groups (optically active or racemic):

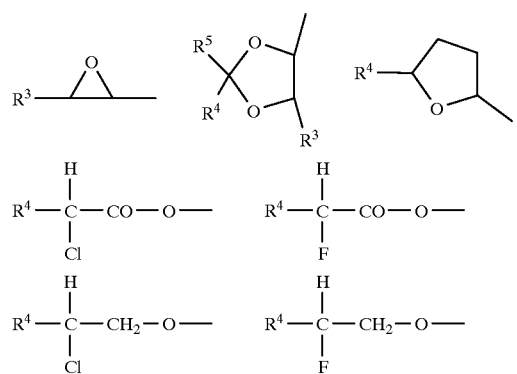

-continued

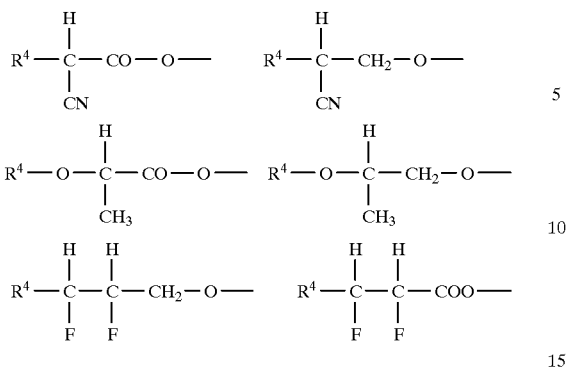

R³, R⁴ and R⁵ are identical or different and are hydrogen or a straight-chain or branched alkyl radical having 1–9 carbon atoms (with or without an asymmetrical carbon atom), where one or more $CH_2$ groups may also be replaced by —O— and/or —CH=CH—, with the proviso that oxygen atoms must not be bonded directly to one another, and/or where one or more H atoms of the alkyl radical may be substituted by —F or —Cl; R⁴ and R⁵ may also together be —$(CH_2)_4$— or —$(CH_2)_5$— if they are bonded to a dioxolane system;

M¹, M², M³, M⁴, M⁵ and M⁶ are identical or different and are —O—, —CO—, —CO—O—, —O—CO—, —O—CO—O—, —$CH_2$—O—, —O—$CH_2$—, —CH=CH— or a single bond;

A¹, A², A³ and A⁴ are identical or different and are 1,4-phenylene, in which one, two or three H atoms may be replaced by F, Cl and/or CN, pyridine2,5-diyl, in which one or two H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or $CH_3$, 1,3,4-thiadiazole-2,5-diyl or naphthalene-2,6-diyl, in which one or two H atoms may be replaced by F, Cl and/or CN;

a, b, c, d, e and f are zero or one, with the proviso that the sum of b, c, d and e is 0, 1 or 2.

Very particular preference is given to compounds of the formula (I) in which the symbols and indices have the following meanings:

R¹ and R² are identical or different and are hydrogen or a straight-chain or branched alkyl radical having 1 to 12 carbon atoms (with or without an asymmetrical carbon atom), where one, two or three $CH_2$ groups may also be replaced by —O—, —O—CO—, —CO—O— or trans-1,4-cyclohexylene, with the proviso that oxygen atoms must not be bonded directly to one another, and/or where one or more H atoms of the alkyl radical may be substituted by —F, or are alternatively one of the following groups (optically active or racemic):

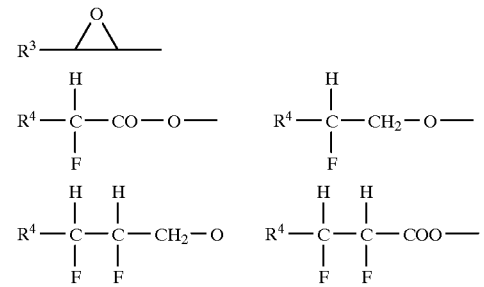

R³ and R⁴ are identical or different and are hydrogen or a straight-chain alkyl radical having 1–9 carbon atoms, where one or more $CH_2$ groups may also be replaced by —O—, with the proviso that oxygen atoms must not be bonded directly to one another;

M¹, M², M³, M⁴, M⁵ and M⁶ are identical or different and are —O—, —CO—O—, —O—CO—, —$CH_2$—O—, —O—$CH_2$—, or a single bond;

A¹, A², A³ and A⁴ are identical or different and are 1,4-phenylene, in which one, two or three H atoms may be replaced by F, pyridine-2,5-diyl, in which one or two H atoms may be replaced by F, pyrimidine-2,5-diyl, trans-1,4-cyclohexylene, in which one or two H atoms may be replaced by CN and/or $CH_3$ or naphthalene-2, 6-diyl, in which one or two H atoms may be replaced by F;

a, b, c, d, e and f are zero or one, with the proviso that the sum of b, c, d and e is 0, 1 or 2.

Especial preference is given to compounds of the formula (I) in which the group (—A¹—M²)$_b$(—A²—M³)$_c$—B—(M⁴—A³)$_d$(—M⁵—A⁴)$_e$ has one of the following meanings:

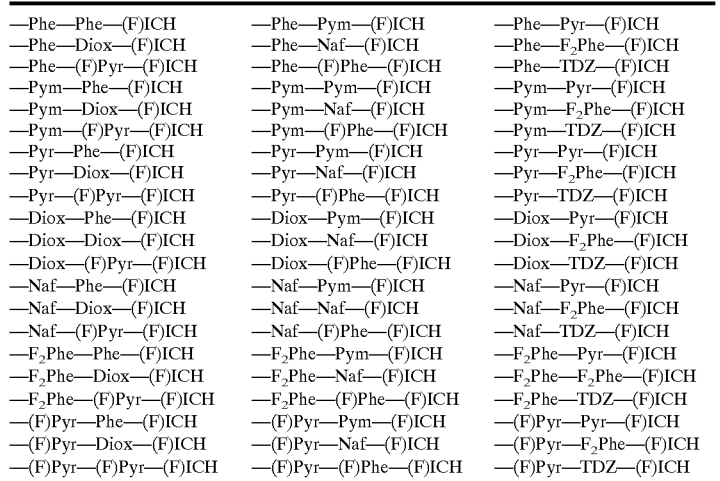

-continued

—(F)Phe—Phe—(F)ICH
—(F)Phe—Diox—(F)ICH
—(F)Phe—(F)Pyr—(F)ICH
—TDZ—Phe—(F)ICH
—TDZ—Diox—(F)ICH
—TDZ—(F)Pyr—(F)ICH
—Phe—(F)ICH
—Diox—(F)ICH
—(F)Pyr—(F)ICH
—(F)ICH—Phe—Phe
—(F)ICH—Diox—Phe
—(F)ICH—(F)Pyr—Phe
—(F)ICH—Phe—Pym
—(F)ICH—Diox—Pym
—(F)ICH—(F)Pyr—Pym
—(F)ICH—Phe—Pyr
—(F)ICH—Diox—Pyr
—(F)ICH—(F)Pyr—Pyr
—(F)ICH—Phe—Diox
—(F)ICH—Diox—Diox
—(F)ICH—(F)Pyr—Diox
—(F)ICH—Phe—Naf
—(F)ICH—Diox—Naf
—(F)ICH—(F)Pyr—Naf
—(F)ICH—Phe—$F_2$Phe
—(F)ICH—Diox—$F_2$Phe
—(F)ICH—(F)Pyr—$F_2$Phe
—(F)ICH—Phe—(F)Pyr
—(F)ICH—Diox—(F)Pyr
—(F)ICH—(F)Pyr—(F)Pyr
—(F)ICH—Phe—(F)Phe
—(F)ICH—Diox—(F)Phe
—(F)ICH—(F)Pyr—(F)Phe
—(F)ICH—Phe—TDZ
—(F)ICH—Diox—TDZ
—(F)ICH—(F)Pyr—TDZ
—(F)ICH—Phe
—(F)ICH—Diox
—(F)ICH—(F)Pyr
—Phe—(F)ICH—Phe
—Diox—(F)ICH—Phe
—(F)Pyr—(F)ICH—Phe
—Phe—(F)ICH—Pym
—Diox—(F)ICH—Pym
—(F)Pyr—(F)ICH—Pym
—Phe—(F)ICH—Pyr
—Diox—(F)ICH—Pyr
—(F)Pyr—(F)ICH—Pyr
—Phe—(F)ICH—Diox
—Diox—(F)ICH—Diox
—(F)Pyr—(F)ICH—Diox
—Phe—(F)ICH—Naf
—Diox—(F)ICH—Naf
—(F)Pyr—(F)ICH—Naf
—Phe—(F)ICH—$F_2$Phe
—Diox—(F)ICH—$F_2$Phe
—(F)Pyr—(F)ICH—$F_2$Phe
—Phe—(F)ICH—(F)Pyr
—Diox—(F)ICH—(F)Pyr
—(F)Pyr—(F)ICH—(F)Pyr
—Phe—(F)ICH—(F)Phe
—Diox—(F)ICH—(F)Phe
—(F)Pyr—(F)ICH (F)Phe
—Phe—(F)ICH—TDZ
—DIOX—(F)ICH—TDZ
—(F)Pyr—(F)ICH—TDZ
—(F)Phe—Pym—(F)ICH
—(F)Phe—Naf—(F)ICH
—(F)Phe—(F)Phe—(F)ICH
—TDZ—Pym—(F)ICH
—TDZ—Naf—(F)ICH
—TDZ—(F)Phe—(F)ICH
—Pym—(F)ICH
—Naf—(F)ICH
—(F)Phe—(F)ICH
—(F)ICH—Pym—Phe
—(F)ICH—Naf—Phe
—(F)ICH—(F)Phe—Phe
—(F)ICH—Pym—Pym
—(F)ICH—Naf—Pym
—(F)ICH—(F)Phe—Pym
—(F)ICH—Pym—Pyr
—(F)ICH—Naf—Pyr
—(F)ICH—(F)Phe—Pyr
—(F)ICH—Pym—Diox
—(F)ICH—Naf—Diox
—(F)ICH—(F)Phe—Diox
—(F)ICH—Pym—Naf
—(F)ICH—Naf—Naf
—(F)ICH—(F)Phe—Naf
—(F)ICH—Pym—$F_2$Phe
—(F)ICH—Naf—$F_2$Phe
—(F)ICH—(F)Phe—$F_2$Phe
—(F)ICH—Pym—(F)Pyr
—(F)ICH—Naf—(F)Pyr
—(F)ICH—(F)Phe—(F)Pyr
—(F)ICH—Pym—(F)Phe
—(F)ICH—Naf—(F)Phe
—(F)ICH—(F)Phe—(F)Phe
—(F)ICH—Pym—TDZ
—(F)ICH—Naf—TDZ
—(F)ICH—(F)Phe—TDZ
—(F)ICH—Pym
—(F)ICH—Naf
—(F)ICH—(F)Phe
—Pym—(F)ICH—Phe
—Naf—(F)ICH—Phe
—(F)Phe—(F)ICH—Phe
—Pym—(F)ICH—Pym
—Naf—(F)ICH—Pym
—(F)Phe—(F)ICH—Pym
—Pym—(F)ICH—Pyr
—Naf—(F)ICH—Pyr
—(F)Phe—(F)ICH—Pyr
—Pym—(F)ICH—Diox
—Naf—(F)ICH—Diox
—(F)Phe—(F)ICH—Diox
—Pym—(F)ICH—Naf
—Naf—(F)ICH—Naf
—(F)Phe—(F)ICH—Naf
—Pyr—(F)ICH—$F_2$Phe
—Naf—(F)ICH—$F_2$Phe
—(F)Phe—(F)ICH—$F_2$Phe
—Pym—(F)ICH—(F)Pyr
—Naf—(F)ICH—(F)Pyr
—(F)Phe—(F)ICH—(F)Pyr
—Pym—(F)ICH—(F)Phe
—Naf—(F)ICH—(F)Phe
—(F)Phe—(F)ICH—(F)Phe
—Pym—(F)ICH—TDZ
—Naf—(F)ICH—TDZ
—(F)Phe—(F)ICH—TDZ
—(F)Phe—Pyr—(F)ICH
—(F)Phe—$F_2$Phe—(F)ICH
—(F)Phe—TDZ—(F)ICH
—TDZ—Pyr—(F)ICH
—TDZ—$F_2$Phe—(F)ICH
—TDZ—TDZ—(F)ICH
—Pyr—(F)ICH
—$F_2$Phe—(F)ICH
—TDZ—(F)ICH
—(F)ICH—Pyr—Phe
—(F)ICH—$F_2$Phe—Phe
—(F)ICH—TDZ—Phe
—(F)ICH—Pyr—Pym
—(F)ICH—$F_2$Phe—Pym
—(F)ICH—TDZ—Pym
—(F)ICH—Pyr—Pyr
—(F)ICH—$F_2$Phe—Pyr
—(F)ICH—TDZ—Pyr
—(F)ICH—Pyr—Diox
—(F)ICH—$F_2$Phe—Diox
—(F)ICH—TDZ—Diox
—(F)ICH—Pyr—Naf
—(F)ICH—$F_2$Phe—Naf
—(F)ICH—TDZ—Naf
—(F)ICH—Pyr—$F_2$Phe
—(F)ICH—$F_2$Phe—$F_2$Phe
—(F)ICH—TDZ—$F_2$Phe
—(F)ICH—Pyr—(F)Pyr
—(F)ICH—$F_2$Phe(F)Pyr
—(F)ICH—TDZ—(F)Pyr
—(F)ICH—Pyr—(F)Phe
—(F)ICH—$F_2$Phe—(F)Phe
—(F)ICH—TDZ—(F)Phe
—(F)ICH—Pyr—TDZ
—(F)ICH—$F_2$Phe—TDZ
—(F)ICH—TDZ—TDZ
—(F)ICH—Pyr
—(F)ICH—$F_2$Phe
—(F)ICH—TDZ
—Pyr—(F)ICH—Phe
—$F_2$Phe—(F)ICH—Phe
—TDZ—(F)ICH—Phe
—Pyr—(F)ICH—Pym
—$F_2$Phe—(F)ICH—Pym
—TDZ—(F)ICH—Pym
—Pyr—(F)ICH—Pyr
—$F_2$Phe—(F)ICH—Pyr
—TDZ—(F)ICH—Pyr
—Pyr—(F)ICH—Diox
—$F_2$Phe—(F)ICH—Diox
—TDZ—(F)ICH—Diox
—Pyr—(F)ICH—Naf
—$F_2$Phe—(F)ICH—Naf
—TDZ—(F)ICH—Naf
—Pyr—(F)ICH—$F_2$Phe
—$F_2$Phe—(F)ICH—$F_2$Phe
—TDZ—(F)ICH—$F_2$Phe
—Pyr—(F)ICH—(F)Pyr
—$F_2$Phe—(F)ICH—(F)Pyr
—TDZ—(F)ICH—(F)Pyr
—Pyr—(F)ICH—(F)Phe
—$F_2$Phe—(F)ICH—(F)Phe
—TDZ—(F)ICH—(F)Phe
—Pyr—(F)ICH—TDZ
—$F_2$Phe—(F)ICH—TDZ
—TDZ—(F)ICH—TDZ where the abbreviations have the following meanings:

(F)ICH: 1-fluoro-5,6,7,8-tetrahydroisoquinoline-3,7-diyl,
Phe: 1,4-phenylene,
Pyr: pyridine-2,5-diyl,
Pym: pyrimidine-2,5-diyl,
Diox: 1,3-dioxane-2,5-diyl,
Naf: naphthalene-2,6-diyl,
F(Phe): fluorobenzene-1,4-diyl,
$F_2$Phe: difluorobenzene-1,4-diyl,
(F)Pyr: fluoropyridine-2,5-diyl and
TDZ: 1,3,4-thiadiazole-2,5-diyl and $M^1$, $M^6$, $R^1$ and $R^2$ are as defined in the formula (I).

Of these, the preferred groups are:

—(F)ICH
—(F)ICH—Naf
—(F)ICH—Phe
—(F)ICH—Pym

—(F)ICH—Pyr
—Naf—(F)ICH
—Naf—(F)ICH—Naf
—Naf—(F)ICH—Phe
—Naf—(F)ICH—Pym
—NAF—(F)ICH—Pyr
—Phe—(F)ICH
—Phe—(F)ICH—Naf
—Phe—(F)ICH—Phe
—Phe—(F)ICH—Pym
—Phe—(F)ICH—Pyr
—Pym—(F)ICH
—Pym—(F)ICH—Naf
—Pym—(F)ICH—Phe
—Pym—(F)ICH—Pym
—Pym—(F)ICH—Pyr
—Pyr—(F)ICH
—Pyr—(F)ICH—Naf
—Pyr—(F)ICH—Phe
—Pyr—(F)ICH—Pym
—Pyr—(F)ICH—Pyr and the following are particularly preferred:

—(F)ICH
—(F)ICH—Naf
—(F)ICH—Phe
—(F)ICH—Pym
—(F)ICH—Pyr
—Naf—(F)ICH
—Phe—(F)ICH
—Pym—(F)ICH
—Pyr—(F)ICH

The compounds according to the invention are prepared by methods known per se from the literature, as described in standard works on organic synthesis, for example Houben-Weyl, Methoden der Organischen Chemie [Methods of Organic Chemistry], Georg-Thieme-Verlag, Stuttgart.

The preparation is carried out under reaction conditions which are known and suitable for said reactions. Use may also be made here of variants which are known per se, but are not described here in greater detail.

If desired, the starting materials can also be formed in situ, by not isolating them from the reaction mixture, but instead immediately converting them further into the compounds of the formula (I).

Scheme 1 shows by way of example a synthetic route to compounds of the formula (I), although other processes are also conceivable and possible.

Scheme 1

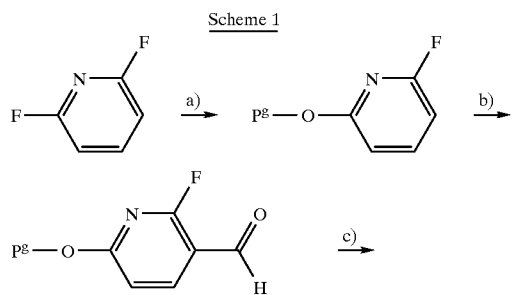

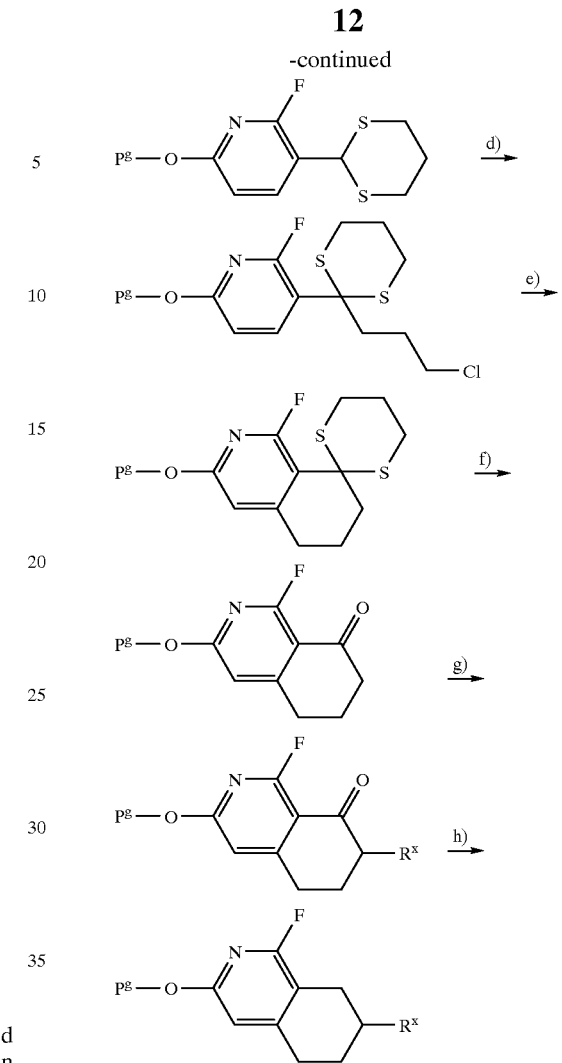

a) Base, P$^g$-OH;
b) 1. LDA (lithium diisopropylamide); 2. DMF (N,N-dimethylformamide); 3. H$^+$; analogous to J. Org. Chem. 51 (1986) 3762;
c) 1,3-Dimercaptopropane, H$^+$; analogous to Synthesis 1969, 17;
d) 1. BuLi; 2. 1-chloro-3-iodopropane; analogous to J. Org. Chem. 33 (1068) 300;
e) eg. AlCl$_3$;
f) eg. HgCl$_2$/MeOH; analogous to Chem. Reviews 49 (1950) 67;
g) 1. Base; 2. R$^x$-X; analogous to Rec. Chem. Prog. 28 (1968) 99;
h) H$_2$N-NH$_2$/KOH; analogous to J. Am. Chem. Soc. 71 (1949) 3301;

The group P$^g$ is the group R$^1$(—M$^1$)$_a$(—A$^1$—M$^2$)$_b$(—A$^2$—M$^3$)$_c$ or a suitable precursor thereof (protected or unprotected) which can be converted into this group in later steps by methods known per se and customary to the person skilled in the art.

For example, P$^g$ can be perfluoroalkylsulfonate, in which case the R$^1$(—M$^1$)$_a$(—A$^1$—M$^2$)$_b$(—A$^2$—M$^3$)$_c$ group is introduced by coupling with, for example, an appropriate boronic acid.

R$^x$ is the (—M$^4$—A$^3$)$_d$(—M$^5$—A$^4$)$_e$(—M$^6$)$_f$—R$^2$ group or a suitable precursor thereof (protected or unprotected), which can be converted into this group in later steps by methods known per se and customary to the person skilled in the art.

The synthesis of the $R^1(-M^1)_a(-A^1-M^2)_b(-A^2-M^3)_c$ or $(-M^4-A^3)_d(-M^5-A^4)_e(-M^6)_f-R^2$ radical is carried out by methods known per se to the person skilled in the art.

The preparation is carried out under reaction conditions which are known and suitable for said reactions. Use may also be made here of variants which are known per se, but are not described here in greater detail.

For example, reference may be made to DE-A 23 44 732, 24 50 088, 24 29 093, 25 02 94, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 03 91 203 for compounds containing pyridine-2,5-diyl groups; DE-A 32 31 462 for compounds containing pyridazine-3,6-diyl groups; EP-A 309 514 for compounds containing 1,3,4-thiadiazole-2,5-diyl groups; WO-A 92/16500 for naphthalene-2,6-diyl groups; DE-A 37 10 890 for bicyclo[2.2.2]octane-1,4-diyl groups; K. Seto et al., Journal of the Chemical Society, Chemical Communications 1988, 56, for dioxoborinane-2,5-diyl groups.

The preparation of disubstituted pyridines, disubstituted pyrazines, disubstituted pyrimidines and disubstituted pyridazines is also given, for example, in the corresponding volumes in the series "The Chemistry of Heterocyclic Compounds" by A. Weissberger and E. C. Taylor (Editors).

Dioxane derivatives are expediently prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example a strong acid, such as sulfuric acid, benzenesulfonic acid or p-toluenesulfonic acid, at temperatures between about 20° C. and about 150° C., preferably between 80° C. and 120° C. Primarily suitable reactive derivatives of the starting materials are acetals.

Some of said aldehydes and 1,3-diols and reactive derivatives thereof are known and some can be prepared without difficulty by standard methods of organic chemistry from compounds known from the literature. For example, the aldehydes are obtainable by oxidation of corresponding alcohols or by reduction of nitriles or corresponding carboxylic acids or derivatives thereof, and the diols are obtainable by reduction of corresponding diesters.

Compounds in which an aromatic ring is substituted by at least one F atom can also be obtained from the corresponding diazonium salts by replacement of the diazonium group by a fluorine atom, for example by the methods of Balz and Schiemann.

As far as the linking of ring systems to one another is concerned, reference may be made, for example to: N. Miyaura, T. Yanagai and A. Suzuki in Synthetic Communications 11 (1981), 513–519; DE—C-39 30 663, M. J. Sharp, W. Cheng, V. Snieckus in Tetrahedron Letters 28 (1987) 5093; G. W. Gray in J. Chem. Soc. Perkin Trans II 1989, 2041 and Mol. Cryst. Liq. Cryst. 172 (1989) 165, 204 (1991) 43 and 91; EP-A 0 449 015; WO-A 89/12039; WO-A 89/03821; EP-A 0 354 434 for the direct linking of aromatics and heteroaromatics; DE-A 32 01 721 for compounds containing —$CH_2CH_2$— bridges, and Koji Seto et al. in Liquid Crystals 8 (1990) 861–870 for compounds containing —C≡C— bridges.

Esters of the formula (I) can also be obtained by esterification of corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known and can be prepared analogously to known processes.

Particularly suitable reactive derivatives of said carboxylic acids are the acid halides, especially the chlorides and bromides, furthermore the anhydrides, for example also mixed anhydrides, azides or esters, in particular alkyl esters having 1–4 carbon atoms in the alkyl group.

Particularly suitable reactive derivatives of said alcohols and phenols are the corresponding metal alkoxides or phenoxides, preferably of an alkali metal, such as sodium or potassium.

The esterification is advantageously carried out in the presence of an inert solvent. Particularly suitable solvents are ethers, such as diethyl ether, di-n-butyl ether, THF (tetrahydrofuran), dioxane or anisole, ketones, such as acetone, butanone or cyclohexanone, amides, such as DMF or hexa-methylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is expediently first converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This can then be reacted with the corresponding alkyl halide, alkyl sulfonate or dialkyl sulfate, expediently in an inert solvent, such as acetone, 1,2-dimethoxy-ethane, DMF or dimethylsulfoxide, or alternatively with an excess of aqueous or aqueous/alcoholic NaOH or KOH at temperatures between about 20° and 1000° C.

Regarding the synthesis of specific radicals $R^1$, reference may additionally be made, for example, to EP-A 0 355 008 for compounds containing silicon-containing side chains and to EP-A 0 292 954 and EP-A 0 398 155 for compounds containing cyclopropyl groups in the side chain.

The provision of compounds of the formula (I) very generally considerably broadens the range of liquid-crystalline substances which are suitable, from various application points of view, for the preparation of liquid-crystalline mixtures.

In this connection, the compounds of the formula (I) have a broad range of applications. Depending on the choice of substituents, they can be used as base materials from which liquid-crystalline phases are predominantly composed; however, compounds of the formula (I) can also be added to liquid-crystalline base materials from other classes of compound, in order, for example, to modify the dielectric and/or optical anisotropy of a dielectric of this type and/or to optimize its threshold voltage and/or its viscosity.

The invention also relates to the use of compounds of the formula (I) in liquid-crystal mixtures, preferably ferroelectric and nematic mixtures, in particular ferroelectric mixtures.

The invention furthermore relates to liquid-crystal mixtures, preferably ferroelectric and nematic mixtures, in particular ferroelectric mixtures, containing one or more compounds of the formula (I).

The liquid-crystal mixtures according to the invention generally contain from 2 to 35, preferably from 2 to 25, particularly preferably from 2 to 20 components.

They generally contain from 0.01 to 80% by weight, preferably from 0.1 to 60% by weight, particularly preferably from 0.1 to 30% by weight, of one or more, preferably 1 to 10, particularly preferably 1 to 5, very particularly preferably 1 to 3, of the compounds of the formula (I) according to the invention.

Further components of liquid-crystal mixtures containing compounds of the formula (I) according to the invention are preferably selected from known compounds having smectic and/or nematic and/or cholesteric phases. These include, for example:

derivatives of phenylpyrimidine, as described, for example, in WO 86/06401 and U.S. Pat. No. 4,874,542, meta-substituted aromatic compounds having a six-membered ring, as described, for example, in EP-A 0 578 054, silicon compounds, as described, for example, in EP-A 0 355 008, mesogenic compounds containing only one side chain as described, for example, in EP-A 0 541 081, hydroquinone derivatives, as described, for example, in EP-A 0 603 786, pyridyipyrimidines, as described, for example, in WO 92/12974, phenylbenzoates, as described, for example, in P. Keller, Ferroelectrics 58 (1984), 3, and J. W. Goodby et al., Liquid Crystals and Ordered Fluids, Vol. 4, New York, 1984, and thiadiazoles as described, for example, in EP-A 0 309 514.

Examples of suitable chiral, non-racemic dopes are:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A 0 351 746, optically active dioxolane esters, as described, for example, in EP-A 0 361 272, optically active tetrahydrofuran-2-carboxylic esters, as described, for example, in EP-A 0 355 561, and optically active 2-fluoroalkyl ethers, as described, for example, in EP-A 0 237 007 and U.S. Pat. No. 5,051,506.

The mixtures can in turn be used in electro-optical or fully optical elements, for example display elements, switching elements, light modulators, elements for image processing and/or signal processing or generally in the area of nonlinear optics.

Liquid-crystalline mixtures containing compounds of the formula (I) are particularly suitable for use in electro-optical switching and display devices (displays). These displays are usually constructed in such a way that a liquid-crystal layer is enclosed on both sides by layers which are usually, in this sequence starting from the LC layer, at least one alignment layer, electrodes and a limiting sheet (for example of glass). In addition, they contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers 1987).

The mixtures are furthermore suitable for field treatment, i.e. for operation in the quasi-bookshelf geometry (QBG) (see, for example, H. Rieger et al., SID 91 Digest (Anaheim), 1991, p. 396).

The novel mixtures are likewise suitable for use in ferroelectric liquid-crystal displays which are based on utilization of the DHF effect or the PSFLCD effect (pitch stabilized ferroelectric liquid-crystal display, also known as SBF, short pitch bistable ferroelectric effect).

In addition, the compounds of the formula (I) can also be used as components of antiferroelectric liquid-crystal mixtures. Reference is expressly made to the literature references cited in this application; by being cited, they are an integral part of the description.

The invention is described in greater detail by means of the examples, but this is not intended to represent a limitation.

EXAMPLE 1

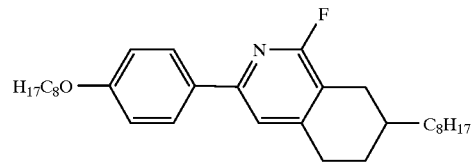

1-Fluoro-3-[4-(octyloxy)phenyl]-7-octyl-5,6,7,8-tetrahydroisoquinoline 10 mmol of 1-fluoro-3-(4-hydroxyphenyl)-7-octyl-5,6,7,8-tetrahydroisoquinoline are dissolved in 50 ml of DMF, and 11 mmol of sodium hydride are added. After the mixture has been stirred for 30 minutes, 11 mmol of 1-octyl bromide are added dropwise, and the mixture is stirred at 60° C. for a further 140 minutes and poured into water. The mixture is extracted with dichloromethane, the combined organic phases are dried, the solvent is removed in vacuo and the residue is chromatographed on silica gel, giving 8 mmol of 1-fluoro-3-[4-(octyloxy)phenyl]-7-octyl-5,6,7,8-tetrahydroisoquinoline.

1-Fluoro-3-(4-hydroxyphenyl)-7-alkyl-5,6,7,8-tetrahydroisoquinolines can be reacted analogously to Example 1 with further alkyl halides, 2-fluoroalkyl sulfonates, 2,3-difluoroalkyl sulfonates, 3-alkyloxirane-2-methyl sulfonates, (ω-bromoalkyl)cyclopropanes or 1-bromodimethylsilanylalkanes.

EXAMPLE 2

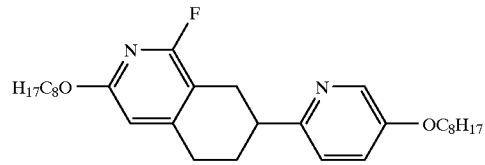

7-[5-(Octyloxy)pyridin-2-yl]-1-fluoro-3-octyloxy-5,6,7,8-tetrahydroisoquinoline 10 mmol of 1-fluoro-7-(5-hydroxypyridin-2-yl)-3-octyloxy-5,6,7,8-tetrahydroisoquinoline are dissolved in 50 ml of DMF, and 11 mmol of sodium hydride are added. After the mixture has been stirred for 30 minutes, 11 mmol of 1-octyl bromide are added dropwise, and the mixture is stirred at 60° C. for a further 140 minutes and poured into water. The mixture is extracted with dichloromethane, the combined organic phases are dried, the solvent is removed in vacuo and the residue is chromatographed on silica gel, giving 7.55 mmol of 7-[5-(octyloxy)pyridin-2-yl]-1-fluoro-3-octyloxy-5,6,7,8-tetrahydroisoquinoline.

1-Fluoro-7-(5-hydroxypyridin-2-yl)-3-octyloxy-5,6,7,8-tetrahydroisoquinolines can be reacted analogously to Example 2 with 2-fluoroalkyl sulfonates, 2,3-difluoroalkyl sulfonates, 3-alkyloxirane-2-methyl sulfonates, (ω-bromoalkyl)cyclopropanes or 1-bromodimethylsilanylalkanes.

EXAMPLE 3

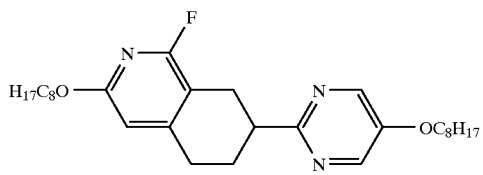

7-[5-(Octyloxy)pyrimidin-2-yl]-1-fluoro-3-octyloxy-5,6,7,8-tetrahydroisoquinoline 10 mmol of 1-fluoro-7-(5-hydroxypyrimidin-2-yl)-3-octyloxy-5,6,7,8-tetrahydroisoquinoline are dissolved in 50 ml of DMF, and 11 mmol of sodium hydride are added. After the mixture has been stirred for 30 minutes, 11 mmol of 1-octyl bromide are added dropwise, and the mixture is stirred at 60° C. for a further 140 minutes and poured into water. The mixture is extracted with dichloromethane, the combined organic phases are dried, the solvent is removed in vacuo, and the residue is chromatographed on silica gel, giving 9 mmol of 7-[5-(octyloxy)pyrimidin-2-yl]-1-fluoro-3-octyloxy-5,6,7,8-tetrahydroisoquinoline.

1-Fluoro-7-(5-hydroxypyrimidin-2-yl)-3-alkyloxy-5,6,7,8-tetrahydroisoquinolines can be reacted analogously to Example 3 with 2-fluoroalkyl sulfonates, 2,3-difluoroalkyl sulfonates, 3-alkyloxirane-2-methyl sulfonates, (ω-bromoalkyl)cyclopropanes or 1-bromodimethylsilanylalkanes.

We claim:
1. A 1-fluoro-5,6,7,8-tetrahydroisoquinoline compound of the formula (I)

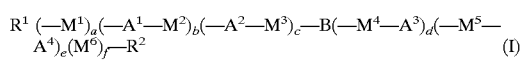

in which the symbols and indices have the following meanings: the group B is

$R^1$ and $R^2$ are identical or different and are hydrogen, —CN, —F, —Cl, —CF$_3$, —CHF$_2$, —CH$_2$F, —OCF$_3$, —OCHF$_2$, —OCH$_2$F or a straight-chain or branched alkyl radical having 1 to 20 carbon atoms (with or without an asymmetrical carbon atom), where one or more CH$_2$ groups may also be replaced by —O—, —S—, —CO—O—, —O—CO—, —O—CO—O—, —CO—, —CS—, —CH=CH—, —C≡C—, cyclopropane-1,2-diyl, —Si(CH$_3$)$_2$—, 1,4-phenylene, trans-1,4-cyclohexylene or trans-1,3-cyclopentylene, with the proviso that oxygen atoms and/or sulfur atoms must not be bonded directly to one another, and/or where one or more H atoms of the alkyl radical may be substituted by —F, —Cl, —Br, —OR$^3$, —SCN, —OCN or —N$_3$ or are alternatively one of the following groups (optically active or racemic):

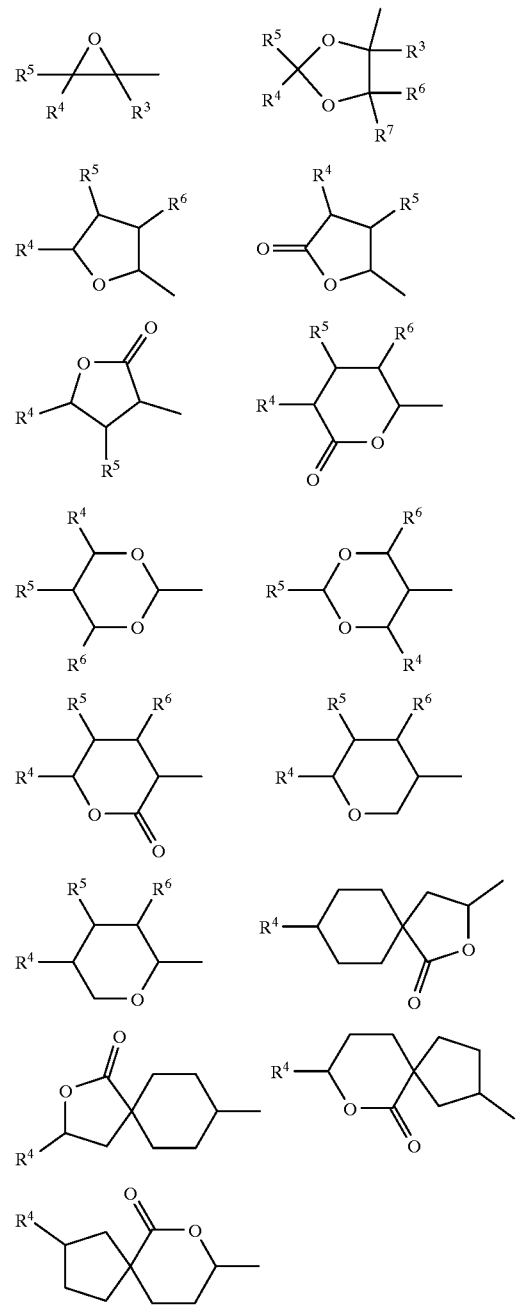

-continued

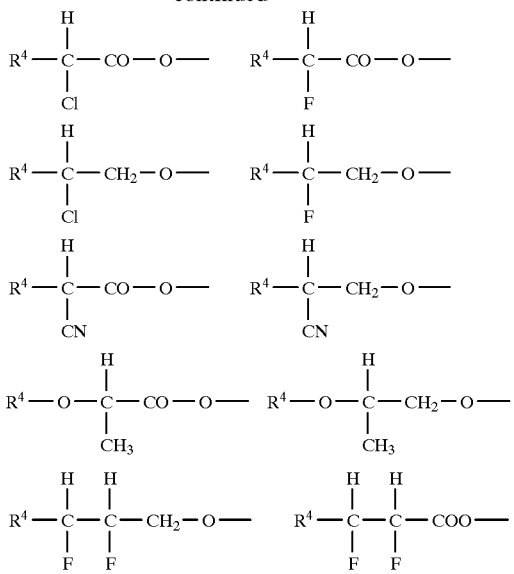

$R^3$, $R^4$, $R^5$, $R^6$ and $R^7$ are identical or different and are hydrogen or a straight-chain or branched alkyl radical having 1–16 carbon atoms (with or without an asymmetrical carbon atom), where one or more $CH_2$ groups may also be replaced by —O— and/or —CH=CH—, with the proviso that oxygen atoms must not be bonded directly to one another, and/or where one or more H atoms of the alkyl radical may be substituted by —F or —Cl; $R^4$ and $R^5$ may also together be —$(CH_2)_4$— or —$(CH_2)_5$— if they are bonded to an oxirane, dioxolane, tetrahydrofuran, tetrahydropyran, butyrolactone or valerolactone system;

$M^1$, $M^2$, $M^3$, $M^4$, $M^5$ and $M^6$ are identical or different and are —O—, —S—, —CO—, —CO—O—, —O—CO—, —O—CO—O—, —CO—S—, —S—CO—, —CS—O—, —O—CS—, —S—CS—S—, —O—CS—O—, —S—CO—S—, —CS—, —$CH_2$—O—, —O—$CH_2$—, —$CH_2$—S—, —S—$CH_2$—, —CH=CH—, —C≡C—, —$CH_2$—$CH_2$—CO—O, —O—CO—$CH_2$—$CH_2$— or a single bond;

$A^1$, $A^2$, $A^3$ and $A^4$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or $CH_3$, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene-2,4-diyl, in which one H atom may be replaced by F, Cl and/or CN, thiophene-2,5-diyl, in which one or two H atoms may be replaced by F, Cl and/or CN, piperazine-1,4-diyl, piperazine-2,5-diyl, naphthalene-2,6-diyl, in which one or more H atoms may be replaced by F, Cl and/or CN, bicyclo[2.2.2]octane-1,4-diyl, in which one or more H atoms may be replaced by F, Cl and/or CN, 1,3-dioxaborinane-2,5-diyl or the group B;

a and f are zero or one; b, c, d, e and f are zero or one wherein at least one radical must be one; with the proviso that the sum of b, c, d and e is 1 or 2.

2. A 1-fluoro-5,6,7,8-tetrahydroisoquinoline compound as claimed in claim 1, wherein the symbols and indices in the formula (I) have the following meanings:

$R^1$ and $R^2$ are identical or different and are hydrogen, —CN, —F, —Cl, —$CF_3$, —$CHF_2$, —$CH_2F$, —$OCF_3$, —$OCHF_2$, —$OCH_2F$ or a straight-chain or branched alkyl radical having 1 to 18 carbon atoms (with or without an asymmetrical carbon atom), where one or more $CH_2$ groups may also be replaced by —O—, —CO—, —CO—O—, —O—CO—, —O—CO—O—, —CH=CH—, —C≡—C—, cyclopropane-1,2-diyl, —$Si(CH_3)_2$— or trans-1,4-cyclohexylene, with the proviso that oxygen atoms must not be bonded directly to one another, and/or where one or more H atoms of the alkyl radical may be substituted by —F, —Cl, —$OR^3$, —OCN or —$N_3$, or are alternatively one of the following groups (optically active or racemic):

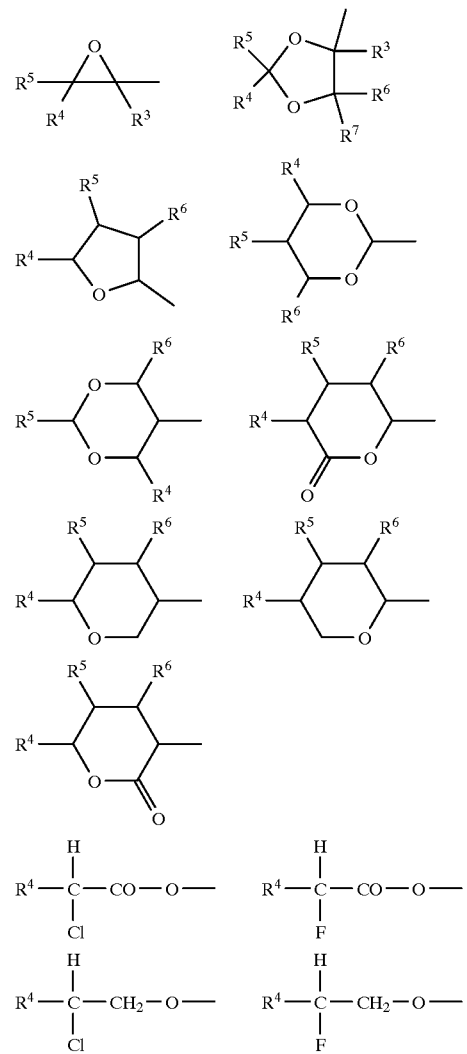

-continued

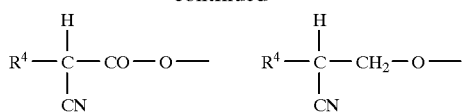

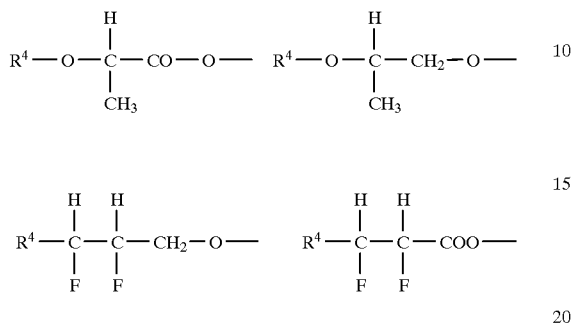

$R^3$, $R^4$, $R^5$, $R^6$ and $R^7$ are identical or different and are hydrogen or a straight-chain or branched alkyl radical having 1–16 carbon atoms (with or without an asymmetrical carbon atom), where one or more $CH_2$ groups may also be replaced by —O— and/or —CH=CH—, with the proviso that oxygen atoms must not be bonded directly to one another, and/or where one or more H atoms of the alkyl radical may be substituted by —F or —Cl; $R^4$ and $R^5$ may also together be —$(CH_2)_4$— or —$(CH_2)_5$— if they are bonded to an oxirane, dioxolane, tetrahydrofuran, tetrahydropyran or valerolactone system;

$M^1$, $M^2$, $M^3$, $M^4$, $M^5$ and $M^6$ are identical or different and are —O—, —CO—, —CO—O—, —O—CO—, —O—CO—O—, —O—CS—O—, —$CH_2$—O—, —O—$CH_2$—, —CH=CH—, —C≡C— or a single bond;

$A^1$, $A^2$, $A^3$ and $A^4$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or $CH_3$, 1,3,4-thiadiazole-2,5-diyl, 1,3-dioxane-2,5-diyl, thiophene-2,4-diyl, in which one H atom may be replaced by F, Cl and/or CN, thiophene-2,5-diyl, in which one or two H atoms may be replaced by F, Cl and/or CN, naphthalene-2,6-diyl, in which one or more H atoms may be replaced by F, Cl and/or CN, or the group B.

3. A 1-fluoro-5,6,7,8-tetrahydroisoquinoline compound as claimed in claim 1, wherein the symbols and indices in the formula (I) have the following meanings:

$R^1$ and $R^2$ are identical or different and are hydrogen, —CN, —F, —Cl, —$CF_3$, —$CHF_2$, —$CH_2F$, —$OCF_3$, —$OCHF_2$, —$OCH_2F$ or a straight-chain or branched alkyl radical having 1 to 16 carbon atoms (with or without an asymmetrical carbon atom), where one, two or three $CH_2$ groups may also be replaced by —O—, —CO—, —O—CO—, —CO—O—, —CH=CH—, cyclopropane-1,2-diyl, —$Si(CH_3)_2$— or trans-1,4-cyclohexylene, with the proviso that oxygen atoms must not be bonded directly to one another, and/or where one or more H atoms of the alkyl radical may be substituted by —F, —Cl or —$OR^3$, or are alternatively one of the following groups (optically active or racemic):

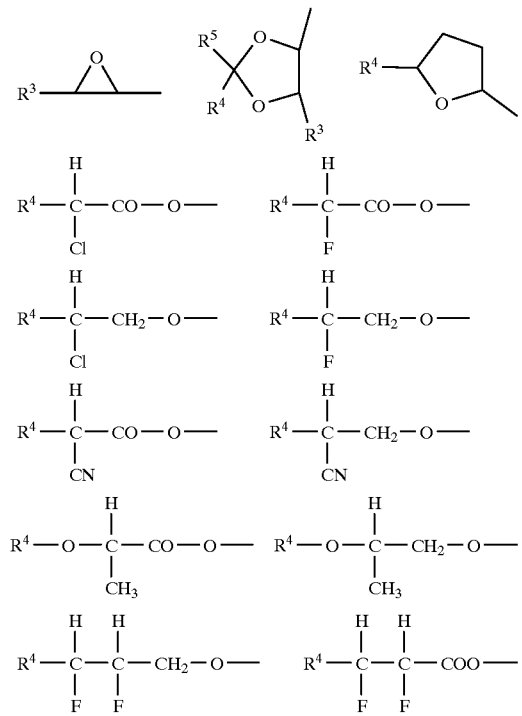

$R^3$, $R^4$ and $R^5$ are identical or different and are hydrogen or a straight-chain or branched alkyl radical having 1–9 carbon atoms (with or without an asymmetrical carbon atom), where one or more $CH_2$ groups may also be replaced by —O— and/or —CH=CH—, with the proviso that oxygen atoms must not be bonded directly to one another, and/or where one or more H atoms of the alkyl radical may be substituted by —F or —Cl; $R^4$ and $R^5$ may also together be —$(CH_2)_4$— or —$(CH_2)_5$— if they are bonded to a dioxolane system;

$M^1$, $M^2$, $M^3$, $M^4$, $M^5$ and $M^6$ are identical or different and are —O—, —CO—, —CO—O—, —O—CO—, —O—CO—O—, —$CH_2$—O—, —O—$CH_2$—, —CH=CH— or a single bond;

$A^1$, $A^2$, $A^3$ and $A^4$ are identical or different and are 1,4-phenylene, in which one, two or three H atoms may be replaced by F, Cl and/or CN, pyridine-2,5-diyl, in which one or two H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or $CH_3$, 1,3,4-thiadiazole-2,5-diyl or naphthalene-2,6-diyl, in which one or two H atoms may be replaced by F, Cl and/or CN.

4. A 1-fluoro-5,6,7,8-tetrahydroisoquinoline compound as claimed in claim 1, wherein the $(-A^1-M^2)_b(-A^2-M^3)_c-B-(M^4-A^3)_d(-M^5-A^4)_e$ group has one of the following meanings:

| | | |
|---|---|---|
| —Phe—Phe—(F)ICH | —Phe—Pym—(F)ICH | —Phe—Pyr—(F)ICH |
| —Phe—Diox—(F)ICH | —Phe—Naf—(F)ICH | —Phe—F$_2$Phe—(F)ICH |
| —Phe—(F)Pyr—(F)ICH | —Phe—(F)Phe—(F)ICH | —Phe—TDZ—(F)ICH |
| —Pym—Phe—(F)ICH | —Pym—Pyr—(F)ICH | —Pym—Pyr—(F)ICH |
| —Pym—Diox—(F)ICH | —Pym—Naf—(F)ICH | —Pym—F$_2$Phe—(F)ICH |
| —Pym—(F)Pyr—(F)ICH | —Pym—(F)Phe—(F)ICH | —Pym—TDZ—(F)ICH |
| —Pyr—Phe—(F)ICH | —Pyr—Pym—(F)ICH | —Pyr—Pyr—(F)ICH |
| —Pyr—Diox—(F)ICH | —Pyr—Naf—(F)ICH | —Pyr—F$_2$Phe—(F)ICH |
| —Pyr—(F)Pyr—(F)ICH | —Pyr—(F)Phe—(F)ICH | —Pyr—TDZ—(F)ICH |
| —Diox—Phe—(F)ICH | —Diox—Pym—(F)ICH | —Diox—Pyr—(F)ICH |
| —Diox—Diox—(F)ICH | —Diox—Naf—(F)ICH | —Diox—F$_2$Phe—(F)ICH |
| —Diox—(F)Pyr—(F)ICH | —Diox—(F)Phe—(F)ICH | —Diox—TDZ—(F)ICH |
| —Naf—Phe—(F)ICH | —Naf—Pym—(F)ICH | —Naf—Pyr—(F)ICH |
| —Naf—Diox—(F)ICH | —Naf—Naf—(F)ICH | —Naf—F$_2$Phe—(F)ICH |
| —Naf—(F)Pyr—(F)ICH | —Naf—(F)Phe—(F)ICH | —Naf—TDZ—(F)ICH |
| —F$_2$Phe—Phe—(F)ICH | —F$_2$Phe—Pym—(F)ICH | —F$_2$Phe—Pyr—(F)ICH |
| —F$_2$Phe—Diox—(F)ICH | —F$_2$Phe—Naf—(F)ICH | —F$_2$Phe—F$_2$Phe—(F)ICH |
| —F$_2$Phe—(F)Pyr—(F)ICH | —F$_2$Phe—(F)Phe—(F)ICH | —F$_2$Phe—TDZ—(F)ICH |
| —(F)Pyr—Phe—(F)ICH | —(F)Pyr—Pym—(F)ICH | —(F)Pyr—Pyr—(F)ICH |
| —(F)Pyr—Diox—(F)ICH | —(F)Pyr—Naf—(F)ICH | —(F)Pyr—F$_2$Phe—(F)ICH |
| —(F)Pyr—(F)Pyr—(F)ICH | —(F)Pyr—(F)Phe—(F)ICH | —(F)Pyr—TDZ—(F)ICH |
| —(F)Phe—Phe—(F)ICH | —(F)Phe—Pym—(F)ICH | —(F)Phe—Pyr—(F)ICH |
| —(F)Phe—Diox—(F)ICH | —(F)Phe—Naf—(F)ICH | —(F)Phe—F$_2$Phe—(F)ICH |
| —(F)Phe—(F)Pyr—(F)ICH | —(F)Phe—(F)Phe—(F)ICH | —(F)Phe—TDZ—(F)ICH |
| —TDZ—Phe—(F)ICH | —TDZ—Pym—(F)ICH | —TDZ—Pyr—(F)ICH |
| —TDZ—Diox—(F)ICH | —TDZ—Naf—(F)ICH | —TDZ—F$_2$Phe—(F)ICH |
| —TDZ—(F)Pyr—(F)ICH | —TDZ—(F)Phe—(F)ICH | —TDZ—TDZ—(F)ICH |
| —Phe—(F)ICH | —Pym—(F)ICH | —Pyr—(F)ICH |
| —Diox—(F)ICH | —Naf—(F)ICH | —F$_2$Phe—(F)ICH |
| —(F)Pyr—(F)ICH | —(F)Phe—(F)ICH | —TDZ—(F)ICH |
| —(F)ICH—Phe—Phe | —(F)ICH—Pym—Phe | —(F)ICH—Pyr—Phe |
| —(F)ICH—Diox—Phe | —(F)ICH—Naf—Phe | —(F)ICH—F$_2$Phe—Phe |
| —(F)ICH—(F)Pyr—Phe | —(F)ICH—(F)Phe—Phe | —(F)ICH—TDZ—Phe |
| —(F)ICH—Phe—Pym | —(F)ICH—Pym—Pym | —(F)ICH—Pyr—Pym |
| —(F)ICH—Diox—Pym | —(F)ICH—Naf—Pym | —(F)ICH—F$_2$Phe—Pym |
| —(F)ICH—(F)Pyr—Pym | —(F)ICH—(F)Phe—Pym | —(F)ICH—TDZ—Pym |
| —(F)ICH—Phe—Pyr | —(F)ICH—Pym—Pyr | —(F)ICH—Pyr—Pyr |
| —(F)ICH—Diox—Pyr | —(F)ICH—Naf—Pyr | —(F)ICH—F$_2$Phe—Pyr |
| —(F)ICH—(F)Pyr—Pyr | —(F)ICH—(F)Phe—Pyr | —(F)ICH—TDZ—Pyr |
| —(F)ICH—Phe—Diox | —(F)ICH—Pym—Diox | —(F)ICH—Pyr—Diox |
| —(F)ICH—Diox—Diox | —(F)ICH—Naf—Diox | —(F)ICH—F$_2$Phe—Diox |
| —(F)ICH—(F)Pyr—Diox | —(F)ICH—(F)Phe—Diox | —(F)ICH—TDZ—Diox |
| —(F)ICH—Phe—Naf | —(F)ICH—Pym—Naf | —(F)ICH—Pyr—Naf |
| —(F)ICH—Diox—Naf | —(F)ICH—Naf—Naf | —(F)ICH—F$_2$Phe—Naf |
| —(F)ICH—(F)Pyr—Naf | —(F)ICH—(F)Phe—Naf | —(F)ICH—TDZ—Naf |
| —(F)ICH—Phe—F$_2$Phe | —(F)ICH—Pym—F$_2$Phe | —(F)ICH—Pyr—F$_2$Phe |
| —(F)ICH—Diox—F$_2$Phe | —(F)ICH—Naf—F$_2$Phe | —(F)ICH—F$_2$Phe—F$_2$Phe |
| —(F)ICH—(F)Pyr—F$_2$Phe | —(F)ICH—(F)Phe—F$_2$Phe | —(F)ICH—TDZ—F$_2$Phe |
| —(F)ICH—Phe—(F)Pyr | —(F)ICH—Pym—(F)Pyr | —(F)ICH—Pyr—(F)Pyr |
| —(F)ICH—Diox—(F)Pyr | —(F)ICH—Naf—(F)Pyr | —(F)ICH—F$_2$Phe—(F)Pyr |
| —(F)ICH—(F)Pyr—(F)Pyr | —(F)ICH—(F)Phe—(F)Pyr | —(F)ICH—TDZ—(F)Pyr |
| —(F)ICH—Phe—(F)Phe | —(F)ICH—Pym—(F)Phe | —(F)ICH—Pyr—(F)Phe |
| —(F)ICH—Diox—(F)Phe | —(F)ICH—Naf—(F)Phe | —(F)ICH—F$_2$Phe—(F)Phe |
| —(F)ICH—(F)Pyr—(F)Phe | —(F)ICH—(F)Phe—(F)Phe | —(F)ICH—TDZ—(F)Phe |
| —(F)ICH—Phe—TDZ | —(F)ICH—Pym—TDZ | —(F)ICH—Pyr—TDZ |
| —(F)ICH—Diox—TDZ | —(F)ICH—Naf—TDZ | —(F)ICH—F$_2$Phe—TDZ |
| —(F)ICH—(F)Pyr—TDZ | —(F)ICH—(F)Phe—TDZ | —(F)ICH—TDZ—TDZ |
| —(F)ICH—Phe | —(F)ICH—Pym | —(F)ICH—Pyr |
| —(F)ICH—Diox | —(F)ICH—Naf | —(F)ICH—F$_2$Phe |
| —(F)ICH—(F)Pyr | —(F)ICH—(F)Phe | —(F)ICH—TDZ |
| —Phe—(F)ICH—Phe | —Pym—(F)ICH—Phe | —Pyr—(F)ICH—Phe |
| —Diox—(F)ICH—Phe | —Naf—(F)ICH—Phe | —F$_2$Phe—(F)ICH—Phe |
| —(F)Pyr—(F)ICH—Phe | —(F)Phe—(F)ICH—Phe | —TDZ—(F)ICH—Phe |
| —Phe—(F)ICH—Pym | —Pym—(F)ICH—Pym | —Pyr—(F)ICH—Pym |
| —Diox—(F)ICH—Pym | —Naf—(F)ICH—Pym | —F$_2$Phe—(F)ICH—Pym |
| —(F)Pyr—(F)ICH—Pym | —(F)Phe—(F)ICH—Pym | —TDZ—(F)ICH—Pym |
| —Phe—(F)ICH—Pyr | —Pym—(F)ICH—Pyr | —Pyr—(F)ICH—Pyr |
| —Diox—(F)ICH—Pyr | —Naf—(F)ICH—Pyr | —F$_2$Phe—(F)ICH—Pyr |
| —(F)Pyr—(F)ICH—Pyr | —(F)Phe—(F)ICH—Pyr | —TDZ—(F)ICH—Pyr |
| —Phe—(F)ICH—Diox | —Pym—(F)ICH—Diox | —Pyr—(F)ICH—Diox |
| —Diox—(F)ICH—Diox | —Naf—(F)ICH—Diox | —F$_2$Phe—(F)ICH—Diox |
| —(F)Pyr—(F)ICH—Diox | —(F)Phe—(F)ICH—Diox | —TDZ—(F)ICH—Diox |
| —Phe—(F)ICH—Naf | —Pym—(F)ICH—Naf | —Pyr—(F)ICH—Naf |
| —Diox—(F)ICH—Naf | —Naf—(F)ICH—Naf | —F$_2$Phe—(F)ICH—Naf |
| —(F)Pyr—(F)ICH—Naf | —(F)Phe—(F)ICH—Naf | —TDZ—(F)ICH—Naf |
| —Phe—(F)ICH—F$_2$Phe | —Pym—(F)ICH—F$_2$Phe | —Pyr—(F)ICH—F$_2$Phe |
| —Diox—(F)ICH—F$_2$Phe | —Naf—(F)ICH—F$_2$Phe | —F$_2$Phe—(F)ICH—F$_2$Phe |
| —(F)Pyr—(F)ICH—F$_2$Phe | —(F)Phe—(F)ICH—F$_2$Phe | —TDZ—(F)ICH—F$_2$Phe |
| —Phe—(F)ICH—(F)Pyr | —Pym—(F)ICH—(F)Pyr | —Pyr—(F)ICH—(F)Pyr |
| —Diox—(F)ICH—(F)Pyr | —Naf—(F)ICH—(F)Pyr | —F$_2$Phe—(F)ICH—(F)Pyr |

-continued

| | | |
|---|---|---|
| —(F)Pyr—(F)ICH—(F)Pyr | —(F)Phe—(F)ICH—(F)Pyr | —TDZ—(F)ICH—(F)Pyr |
| —Phe—(F)ICH—(F)Phe | —Pym—(F)ICH—(F)Phe | —Pyr—(F)ICH—(F)Phe |
| —Diox—(F)ICH—(F)Phe | —Naf—(F)ICH—(F)Phe | —$F_2$Phe—(F)ICH—(F)Phe |
| —(F)Pyr—(F)ICH—(F)Phe | —(F)Phe—(F)ICH—(F)Phe | —TDZ—(F)ICH—(F)Phe |
| —Phe—(F)ICH—TDZ | —Pym—(F)ICH—TDZ | —Pyr—(F)ICH—TDZ |
| —Diox—(F)ICH—TDZ | —Naf—(F)ICH—TDZ | —$F_2$Phe—(F)ICH—TDZ |
| —(F)Pyr—(F)ICH—TDZ | —(F)Phe—(F)ICH—TDZ | —TDZ—(F)ICH—TDZ | where the abbreviations have the following meanings:
(F)ICH: 1-fluoro-5,6,7,8-tetrahydroisoquinoline-3,7-diyl,
Phe: 1,4-phenylene,
Pyr: pyridine-2,5-diyl,
Pym: pyrimidine-2,5-diyl,
Diox: 1,3-dioxane-2,5-diyl,
Naf: naphthalene-2,6-diyl,
$F_2$Phe: difluorobenzene-1,4-diyl,
F(Phe): fluorobenzene-1,4-diyl,
(F)Pyr: fluoropyridine-2,5-diyl and
TDZ: 1,3,4-thiadiazole-2,5-diyl
and $M^1$, $M^6$, $R^1$ and $R^2$ are as defined in the formula (I).

5. A liquid-crystal mixture comprising one or more compounds of the formula (I) as claimed in claim 1.

6. A liquid-crystal mixture as claimed in claim 5, which is ferroelectric.

7. A liquid-crystal mixture as claimed in claim 5, which comprises from 0.1 to 60 mol % of one or more compounds of the formula (I).

8. A liquid-crystal mixture as claimed in claim 5, which comprises from 1 to 10 compounds of the formula (I).

9. A switching and/or display device comprising outer plates, electrodes, at least one polarizer, at least one alignment layer and a liquid-crystalline medium, wherein the liquid-crystalline medium is a liquid-crystal mixture as claimed in claim 5.

* * * * *